United States Patent [19]

Lunn et al.

[11] Patent Number: 4,999,235
[45] Date of Patent: Mar. 12, 1991

[54] CONFORMABLE, STRETCHABLE SURGICAL WOUND CLOSURE TAPE

[75] Inventors: Anthony C. Lunn, Princeton; Frank V. Mattei, Piscataway, both of N.J.

[73] Assignee: Ethicon, Inc., Somerville, N.J.

[21] Appl. No.: 387,438

[22] Filed: Jul. 27, 1989

Related U.S. Application Data

[63] Continuation of Ser. No. 77,544, Jul. 24, 1987, abandoned.

[51] Int. Cl.⁵ .............................................. B32B 33/00
[52] U.S. Cl. .................................. 428/156; 128/155; 128/156; 428/172; 428/290; 428/296; 428/343
[58] Field of Search ............... 428/290, 343, 355, 296, 428/156, 172; 427/208.4; 128/156, 155

[56] References Cited

U.S. PATENT DOCUMENTS

| | | | |
|---|---|---|---|
| 3,542,634 | 11/1970 | Such et al. | 428/343 |
| 3,692,618 | 9/1972 | Dorschner et al. | 161/72 |
| 3,855,046 | 12/1974 | Hansen et al. | 161/150 |
| 3,908,650 | 9/1975 | Dunshee et al. | 428/317.7 |
| 3,991,754 | 11/1976 | Gertzman | 128/156 |
| 4,302,500 | 11/1981 | Flora | 128/156 |
| 4,306,929 | 12/1981 | Menikheim et al. | 428/296 |
| 4,379,192 | 5/1983 | Wahlquist et al. | 428/156 |
| 4,612,230 | 9/1986 | Liland et al. | 428/172 |
| 4,622,259 | 11/1986 | McAmish et al. | 428/296 |
| 4,678,703 | 7/1987 | Shibasaki et al. | 428/296 |
| 4,690,859 | 9/1987 | Porter et al. | 428/307.3 |

*Primary Examiner*—Paul J. Thibodeau

[57] ABSTRACT

There is disclosed a wound closure tape comprising a nonwoven fabric having a pressure-sensitive adhesive uniformly disposed over one surface thereof. The tape is strong enough to hold minor wounds closed, and yet will conform to skin contours and will permit flexing and bending without undue restraint or detachment of the tape. The nonwoven fabric employed in the invention is a web of continuous filaments that are randomly oriented in the plane of the fabric, with the filaments being essentially free of bonding at cross-over points (that is, at points of intersection), and wherein the fabric is emboss bonded in an intermittent pattern.

6 Claims, 4 Drawing Sheets

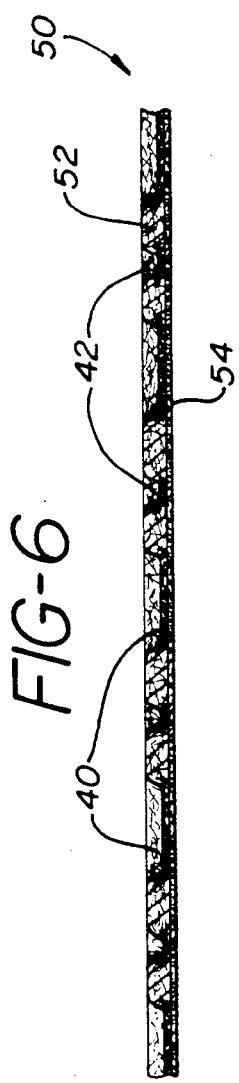
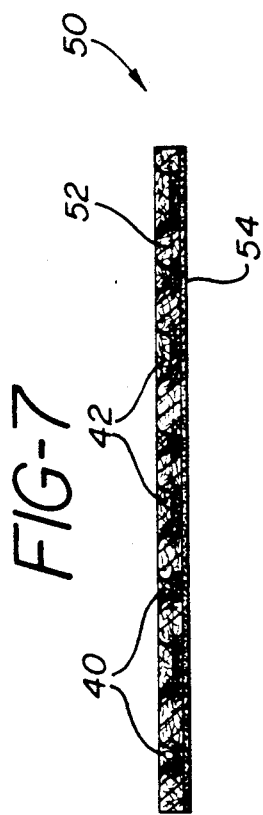
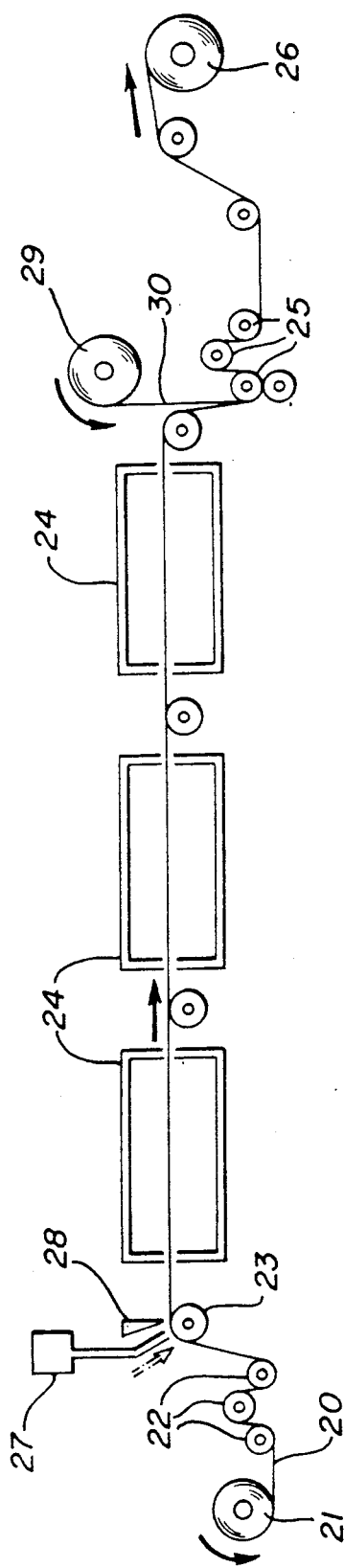

CONFORMABLE, STRETCHABLE SURGICAL WOUND CLOSURE TAPE

This is a continuation of application Ser. No. 77,544, filed July 24, 1987, now abandoned.

The invention relates to pressure-sensitive adhesive tapes, and more particularly to such tapes that have utility in closing wounds.

BACKGROUND OF THE INVENTION

Pressure-sensitive adhesive tapes have been known for some time. Such tapes have gained wide acceptance for closing minor wounds or covering abrasions. Microporous or breathable pressure-sensitive surgical tapes have been developed that have been used in conjunction with sutures to close major wounds. (As used herein, the term "wound" includes surgical incisions.) Also, in certain instances the wound is initially closed with sutures or staples that are removed a few days after surgery, and the wound is then held closed with surgical tape. Such a practice allows drainage of the wound and very often improves the cosmetic results of the surgery. Representative examples of breathable pressure-sensitive adhesive tapes are disclosed in U.S. Pat. Nos. 3,908,650; 3,991,754; and 4,302,500.

While surgical wound closure tapes have been greatly improved over the years in that they have been made of microporous materials which will allow the wound to breath and will allow water to escape from the wound and, hence, eliminate maceration of the wound, none of these prior art tapes have gained wide acceptance for being the primary mechanism for closing major wounds. It is believed that to be a primary wound closure tape, the tape should have good and controlled elastic properties; that is, it must have some give or elasticity so that it will move with the tissue surrounding the wound during normal motion of the body but not so much elasticity that it will allow the wound to open during such normal motion. The tape must also drape; that is, it must have excellent conformability to the area to which it is adhered. It is believed that this is also important to maintain good wound closure. The tape should have good abrasion resistance and tear strength. The tape should also be permeable to water vapor; that is, it should be porous and breathable and not cause maceration of the wound area. The tape should have good adhesive strength and not curl at its edges.

It is an object of the invention to provide a wound closure tape that may be used in conjunction with sutures or staples to close wounds and also may be used in some cases (such as in plastic and minor surgery) as a primary closure for a wound. It is a further object of the invention to provide a wound closure tape that has excellent drape and the required controlled elastic recovery. It is a further object of the invention to provide a tape that will not curl at the edges, has excellent tensile and strength properties, and good abrasion resistance. Another object of the invention is to provide a surgical tape that provides excellent comformability to skin contours, that allows flexing and bending of the body (limbs, fingers, etc.) without undue restraint or detachment of the tape while maintaining accurate approximation of the wound margins. Still another object of the invention is to provide a tape that can be manufactured easily and economically. Other objects of the invention will be readily apparent from the ensuing description and claims.

BRIEF SUMMARY OF THE INVENTION

The invention provides a wound closure tape comprising a nonwoven fabric having a pressure-sensitive adhesive uniformly disposed over one surface thereof. The tape is strong enough to hold minor wounds closed, and yet will conform to skin contours and will permit flexing and bending without undue restraint or detachment of the tape. The nonwoven fabric employed in the invention is a web of continuous filaments that are randomly oriented in the plane of the fabric, with the filaments being essentially free of bonding at cross-over points (that is, at points of intersection), and wherein the fabric is emboss bonded in an intermittent pattern.

THE PRIOR ART

Liland et al., in U.S. Pat. No. 4,612,230, disclose a surgical wound closure tape comprising a substrate of conventional spun bonded nonwoven fabric having a pressure-sensitive adhesive on one face. The continuous filaments that comprise the spunbonded fabric of Liland et al. are bonded at the points where the filaments cross over one another, and the fabric is embossed with a plurality of indentations over the surface.

BRIEF DESCRIPTION OF THE DRAWINGS

FIG. 6 is a cross-sectional view taken along line 6—6 of FIG. 5;

FIG. 7 is a cross-sectional view taken along line 7—7 of FIG. 5; and

FIG. 8 is a schematic diagram of an arrangement of apparatus that can be used to produce the wound closure tapes of the invention.

DETAILED DESCRIPTION OF THE INVENTION

The major novelty of this invention resides in the nonwoven fabric used as the substrate for the wound closure tape. The substrate is a spunbonded nonwoven fabric that has stress properties such that the tape will allow flexing and bending of the body without undue restraint or detachment of the tape while, at the same time, will maintain accurate approximation of the wound margins. Spunbonded nonwoven fabrics comprise a web of continuous filaments that are randomly oriented in the plane of the web. In the usual case, spunbonded fabrics are held together by bonds at the crossover points where the filaments intersect or cross over one another. The spunbonded fabric used in this invention is free of bonds at the cross-over points. Rather, the spunbonded fabrics used in this invention are emboss bonded in an intermittent pattern. The emboss bonding provides the integrity to hold the fabric together.

Figure 1:
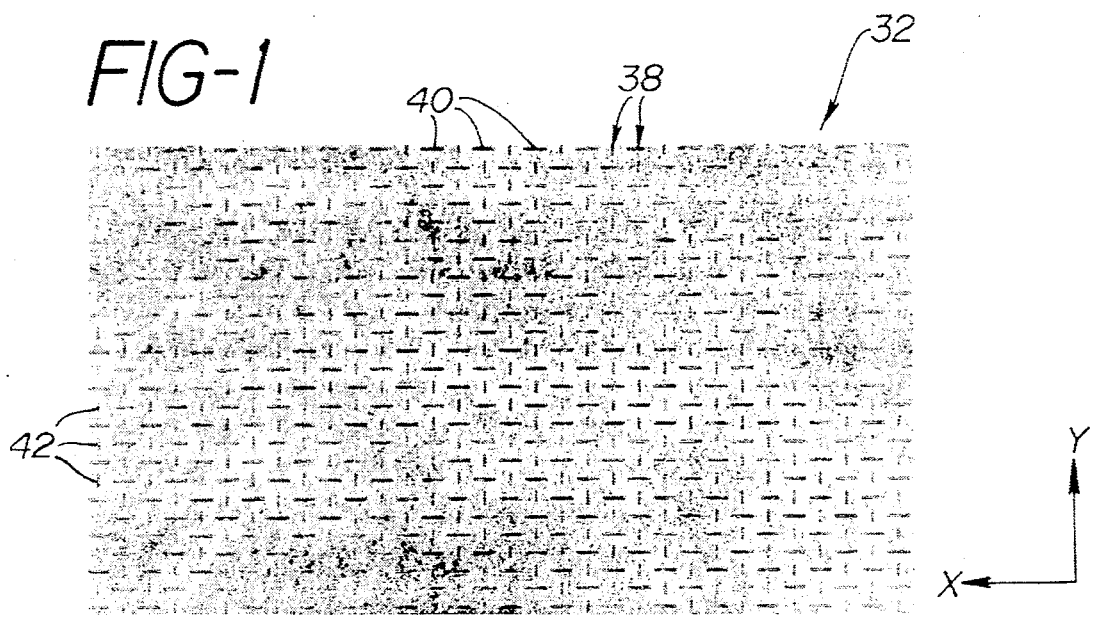
FIGS. 1 and 2 are optical micrographs at 1.33X and 5X magnification of a preferred nonwoven fabric that is used as the substrate in the wound closure tape of the invention.
Figure 2:
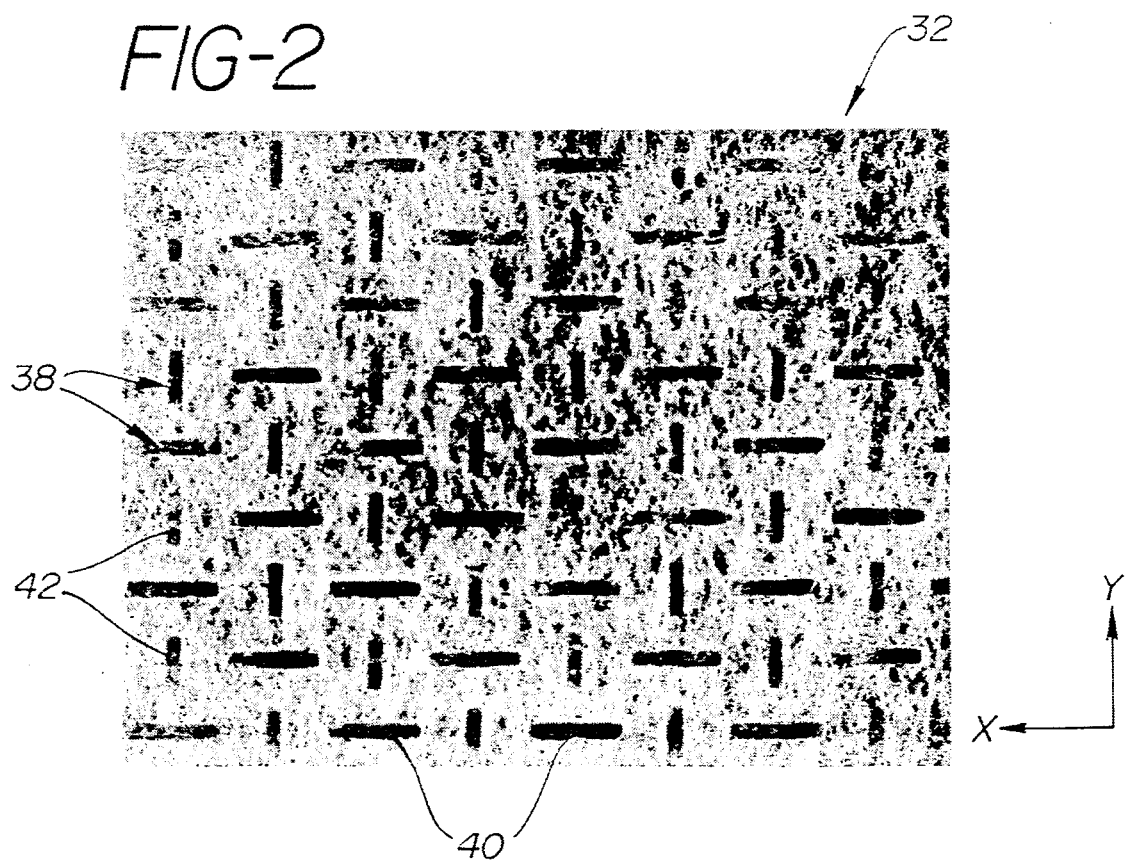
Figure 3:
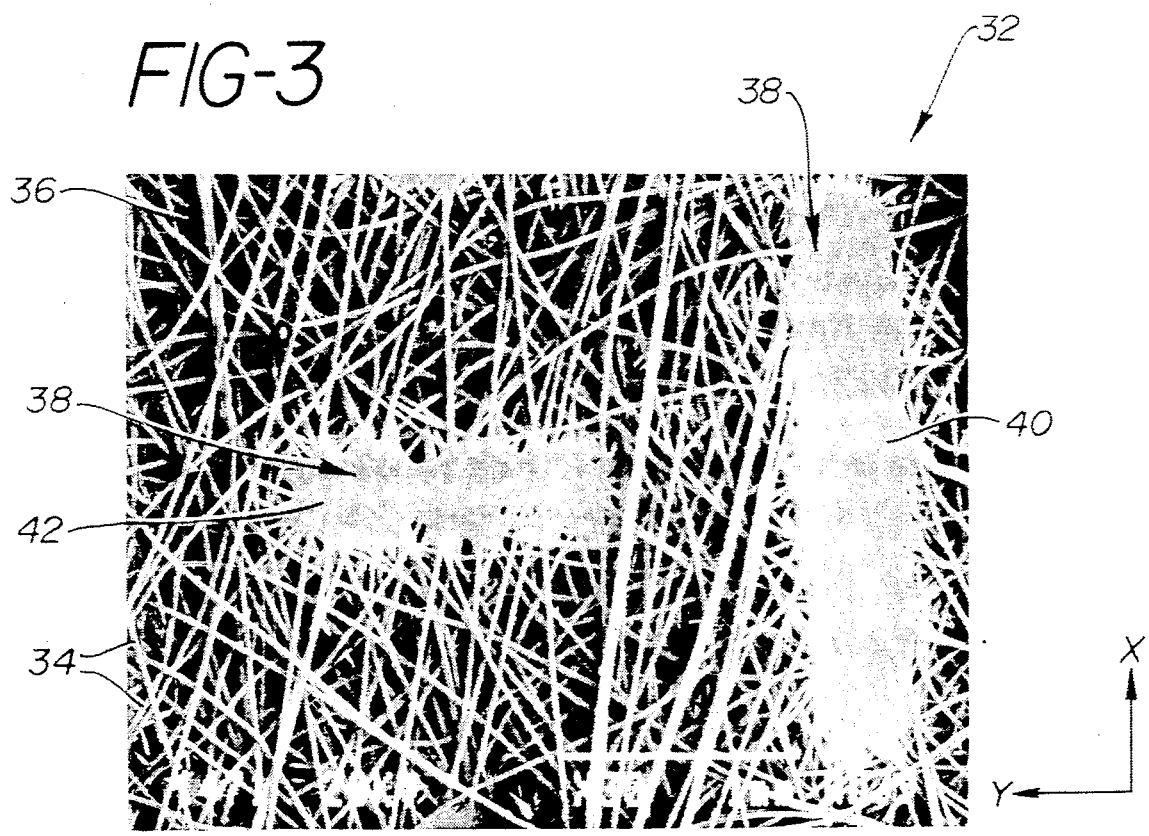
FIG. 3 is a scanning electron micrograph at 30X magnification of the same nonwoven fabric.
Figure 4:
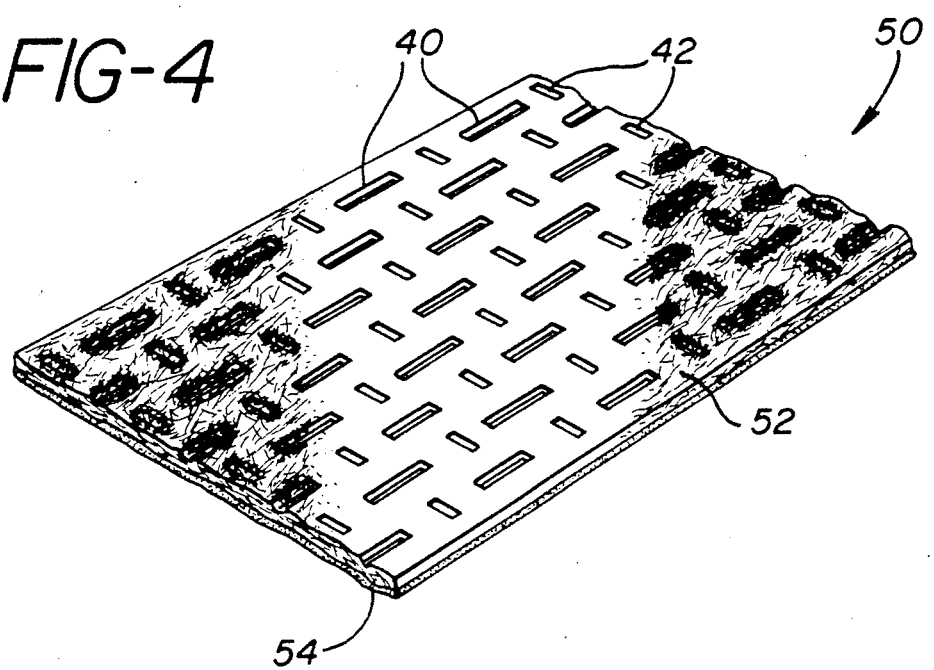
FIG. 4 is a perspective view of a preferred embodiment of the wound closure tape of the invention.
Figure 5:
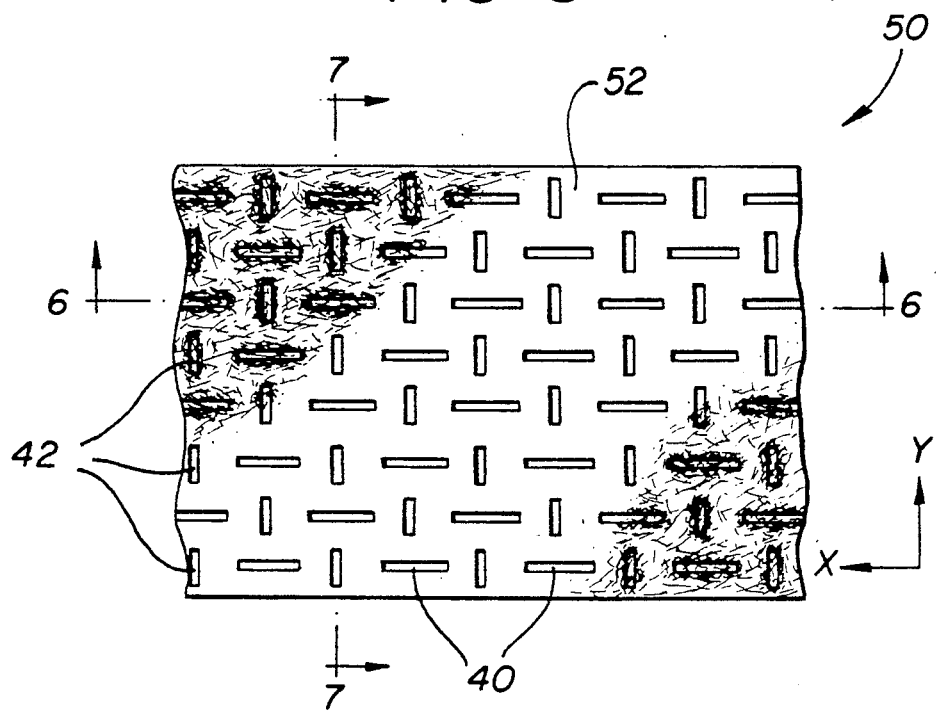
FIG. 5 is an enlarged top plan view of the tape of FIG. 4.

FIGS. 1-3 are optical (FIGS. 1-2) and scanning electron micrographs of one preferred fabric used in the invention. (It is marketed under the trade name of "Cerex 30".) The micrographs are made at 1.33X, 5X, and 30X magnification, respectively. The fabric is designated as 32. The continuous, randomly oriented filaments 34 are not bonded to each other at the cross-over points. Thus, there are significant areas 36 that are essentially free of any bonding. In this preferred embodiment, the fabric is emboss bonded in a pattern of isolated rectangular areas 38. The bonded areas 38 are isolated in this preferred embodiment, that is, they do not touch one another. In the preferred version of the invention that is shown in the drawings, the embossed areas 38 are generally rectangular in shape, with the individual rectangles 40, 42 having one dimension longer than the other, and with the rectangles being arranged so that rectangles 40 whose long dimensions are oriented in one direction ("X") alternate in both the X and Y directions with rectangles 42 whose long dimensions are oriented in a direction ("Y") perpendicular to the direction of the first group of rectangles. This can be seen most clearly in FIGS. 1 and 2 and in FIG. 5, which is a top plan view of a preferred wound closure tape of the invention.

The spunbonded fabric that is the preferred substrate for use in the tapes of the invention can be made by known spunbonding processes, followed by a thermal embossing step to produce the intermittent pattern of embossed areas. The ordinary worker in the nonwoven fabric arts knows how to make such a fabric. The fabrics may be made from polyolefinfilaments (such as polypropylene or polyethylene), polyester filaments, nylon (polyamide) filaments, or mixtures thereof. Preferably, the fabric used in the invention is composed of nylon filaments.

A preferred wound closure tape of the invention is shown in FIGS. 4-7. The tape 50 comprises the fabric substrate 52 having a pressure-sensitive adhesive layer 54 coated uniformly over one surface of the substrate 52. Any of the non-toxic pressure-sensitive adhesives which are permeable to gas and water vapor may be used. Pressure-sensitive adhesives are adhesives which are inherently tacky, visco-elastic, and cohesive in the normal dry state and which are also non-toxic, non-irritating, and suitable for use in surgical, dermatological, or cosmetic applications. Such products are known in the art. Some examples of representative materials suitable for use as adhesive coatings on surgical tapes are given in U.S. Pat. No. 3,645,835. Suitable examples are blends containing polyvinyl ether, acrylic polymers, hydroxy acrylate polymers, polyethers, and acrylate ester copolymers containing hydrophilic groups. Other suitable adhesives include rubber based adhesives such as polyisobutylene and mixtures of polyisobutylene with natural rubber, and the rubbery copolymer of isooctyl acrylate and acrylic acid as described in U.S. Pat. Nos. 2,884,126 and 3,121,021.

The adhesive coating should be porous and should be uniformly disposed over the surface of the fabric substrate. Generally, the adhesive coating is relatively continuous. The adhesive is preferably applied to the substrate at a level of about 1 to 2.5 ounces per square yard. Application is conveniently accomplished by a transfer process wherein the adhesive formulation is spread on a release coated paper, dried, and then contacted with the substrate with sufficient pressure to insure good bonding. The release paper is usually kept in contact with the adhesive to serve as a release strip to be removed from the surgical tape just before use. The fabric/adhesive/release paper laminate is cut up into the desired size, packaged, and sterilized by known procedures. The example, below, illustrates one method of producing the surgical wound closure tapes of the invention.

It should be pointed out that certain substrates, especially in dry atmospheres, will develop a static charge. Hence, when using some substrate materials such as nylon it is desirable to place a surface treatment of an anti-static agent on the substrate before the pressure sensitive adhesive is applied.

To coat the tape with a pressure sensitive adhesive, a line, as schematically shown in FIG. 8, is strung with a release paper 20. The paper is taken from a feed roll 21, passed through tensioning roller guides 22, then over an adhesive supply roll 23, through curing ovens 24 to a laminating roller 25, and finally to a bulk roll wind-up 26. As the release paper passes over the adhesive supply roll 23 the adhesive is foamed using an Oakes foaming unit 27 to a density of about 4½ pounds per gallon (the customary density expression used by coating chemists—for comparison, the density of water is 8.345 pounds per gallon), and is then spread on the release paper. A knife edge 28 is adjusted to provide the desired thickness and amount of adhesive. The adhesive and release paper pass through curing ovens 24 held at temperatures of from about 100° F. to 215° F. to slowly evaporate solvent from the adhesive. The adhesive "tack" properties are monitored to ensure a bond with the backing substrate. The fabric substrate 30 is applied to the surface of the adhesive. The release paper, adhesive, and fabric substrate pass through the laminating rolls 25 and the laminate is then wound on a wind-up roll 26. The laminate is then slit, cut, and packaged as is well known in the art to produce the desired wound closure tape.

EXAMPLE 1

A non-allergenic, non-toxic pressure sensitive acrylic emulsion was knife coated continuously onto 500 yards of a 61 inch wide 90 lb. Poly-Slik release paper. The coated paper was pulled through a series of gas fired drying ovens and was wound up on a single roll. The acrylic emulsion was foamed with air by passing it through an Oakes foamer followed by feeding to the knife coater at such a rate as to give an adhesive film weight of 2 oz/yd$^2$ on a dry basis. Afterwards, the adhesive weight was determined to be 1.8 oz/yd$^2$. After the release paper had been coated, dried, and rolled up, it was mated to 500 yards of 59 inch wide Cerex 30* that was previously anti-stat treated. The Cerex weight was 1 oz/yd$^2$. Cerex 30 was the pattern bonded fabric described above (and shown in FIGS. 1-3) wherein bonding was present only at the points of embossing and not at the fiber/fiber cross-over points. The machine direction corresponds to the "X" direction shown in the drawings. Mating into a 3 layer laminate of Cerex/adhesive/release paper was achieved by passing the release paper with its adhesive coating together with the Cerex through nip rolls at a pressure selected so as to bond the adhesive firmly to the Cerex without pushing it through the other side of the Cerex.

The full width master roll of laminate was then slit into an assortment of rolls of 2 inch and 1⅜ inch

---

*Cerex is James River Corp's trade name for spun-bonded nylon 6,6.

widths. In turn these were score cut and processed on a model 810 Mark Andy die cutting machine so as to give surgical tapes mounted on cards (the "cards" comprising the release paper) with 2 sizes of surgical tapes, namely, ½"×4", and ¼"×3". These tapes mounted on cards were then packaged and sterilized by exposure to a standard ethylene oxide cycle. Test results are shown in Table I.

TABLE I

| TEST | ¼" × 3" STRIP | ½" × 4" STRIP |
|---|---|---|
| 1. Peel Strength From Glass Slides | 2.18 lbs/inch | 2.23 lbs/inch |
| 2. Rolling Ball Tack | — | 0.48 inch |
| 3. Breaking Strength | 15.75 lbs/inch | 15.66 lbs/inch |
| 4. Elongation At Break | 84% | 93% |
| 5. Air Porosity | — | 1.6 sec/100 cc |
| 6. Adhesive Mass Weight, Determined Analytically | — | 1.8 oz/yd$^2$ |

An explanation of the procedures for the tests shown in TABLE I is the following:

1. Peel Strength From Glass Slides

A surgical wound closure tape is adhered to a solvent washed and dried smooth 75×25 mm standard microscope slide using a 10 pound weight. (The weight, in the form of a cylindrical disk, is rolled once over the tape.) The force to peel the tape from the slide is measured with an Instron laboratory tester using a jaw separation rate of 1 inch per minute. The measured force is divided by the width of the tape to yield the peel strength in pounds/inch. The peeling force applied is parallel to the adhered tape.

The far end of the adhered tape is grasped, and the tape is peeled back.

2. Rolling Ball Tack

This is an inclined plane tester in which a standard ball weighing 5.6 grams and having a diameter of 0.437 inch is allowed to run down a 6½ inch long grooved aluminum raceway held at an angle of 22° from the horizontal onto a surgical wound closure tape, adhesive side up. The distance in inches that the ball travels on the adhesive before it stops is measured—the shorter the distance, the more effective is the adhesive tack.

3. and 4. Breaking Strength and Elongation At Break

A standard Instron tensile tester is used to determine these properties in the direction parallel to the long axis of the tape (i.e., the machine direction, which is the "X" direction of the tape shown in the drawings). The chart speed is 10 inches/min, the crosshead speed is 1 inch/min, and the gauge length is 1 inch. The gripping jaws are wide enough to grip the whole width of a ½ inch wide tape.

5. Air Porosity

A Gurley Air Porosity Tester was used. The number of seconds to pass 100 cc of air at low pressure through a surgical tape having an area of 1 in$^2$ is reported. The number shown is not critical; the significance is that the tape is breathable.

6. Adhesive Mass Weight

Several surgical tapes are weighed and are then given several acetone washes to remove the adhesive. After drying, the tapes are weighed again; the difference is the weight of adhesive, which is converted to ounces of adhesive per square yard.

The samples in Table I were also evaluated on humans by a testing company that routinely handles panel evaluations of consumer and medical products. Results of this evaluation are summarized in Table II:

TABLE II

EVALUATION ON HUMANS
COMPARISON OF ½" × 4" TAPE OF
THIS INVENTION (EXAMPLE)
VS. ½" × 4" COMMERCIAL TAPE (CONTROL)
TEST OF ADHESION IN LOWER BACK AREA

|  | % ADHESION** | PEEL FORCE*** |
|---|---|---|
| 1. 24 Hour Reading | | |
| Example 1 | 89% | — |
| Control | 68% | — |
| 2. 48 Hour Reading | | |
| Example 1 | 90% | — |
| Control | 45% | — |
| 3. 72 Hour Reading | | |
| Example 1 | 80% | 196 grams |
| Control | 29% | 58 grams |

**These values (which are the means of 48 samples) are based on the area of the tape that remains adhered to the skin at the time periods shown
***The peel force is the force in grams required to peel the tape off the skin.

EXAMPLES 2 and 3

Table III summarizes data based on runs made at another time using methods similar to the ones explained above in connection with Table I.

TABLE III*

| | | Breaking Strength | Elongation At Break | Adhesion To Glass-Peel Strength | Rolling Ball Tack | Stress @20% Elongation |
|---|---|---|---|---|---|---|
| 1. Example 2 | ½ × 4" | 13.9 lbs/inch | 104% | 1.68 lbs/inch | 0.45 inch | 6 lbs/inch |
| Low bond, pattern embossed Cerex tape of this invention 1 oz/yd$^2$ 1.5 oz/yd$^2$ Adhesive | ¼ × 3" | 12.4 lbs/inch | 94% | 1.76 lbs/inch | | 5.6 lbs/inch |
| 2. Example 3 | ½ × 4" | 15.2 lbs/inch | 93% | 2.0 lbs/inch | 0.325 inch | 7 lbs/inch |
| Low bond, pattern embossed Cerex tape of this invention 1 oz/yd$^2$ 2.0 oz/yd$^2$ Adhesive | ¼ × 3" | 10.4 lbs/inch | 78% | 2.04 lbs/inch | | 5.6 lbs/inch |
| 3. Control 2** | ½ × 4" | 15.8 lbs/inch | 65% | 2.04 lbs/inch | 0.45 inch | 9.2 lbs/inch |
| Standard High Bond Cerex tape, 1 oz/yd$^2$ 1.5 oz/yd$^2$ Adhesive | ¼ × 3" | 15.9 lbs/inch | 60% | 2.08 lbs/inch | | 10 lbs/inch |
| 4. Commercial Control | ½ × 4" | 26.9 lbs/inch | 77% | 0.36 lbs/inch | 0.475 inch | 21 lbs/inch |

TABLE III*-continued

|  | Breaking Strength | Elongation At Break | Adhesion To Glass-Peel Strength | Rolling Ball Tack | Stress @20% Elongation |
|---|---|---|---|---|---|
| ¼ × 3" | 25.5 lbs/inch | 64% | 0.44 lbs/inch |  | 22 lbs/inch |

*All data in Table III is based on ethylene oxide sterilized samples.
**Tape of Liland et al., U.S. Pat. No. 4,612,230

The stress at 20% elongation is taken off the chart used for breaking strength and elongation at break. It is the stress in pounds per inch of width to stretch the tape 20%. The tapes of this invention, in ¼ inch to ½ inch widths, preferably exhibit stresses at 20% elongation of from about 4 to 8 pounds per inch of width.

The surgical tapes of this invention remain adhered to the skin despite normal flexing of body parts and other motion, and in this respect the subject tapes are significantly better than the two controls. An important reason for this is the lower stress required to elongate the subject tapes, as is exemplified by the lower stress at 20% elongation, compared with the two controls. If the stress at 20% elongation were too low, however, the tapes of the invention would not be able to keep the edges of the wound in close approximation. For this reason, a minimum stress of about 4 lbs/in at 20% elongation is preferred.

An additional advantage of the surgical wound closure tapes of the invention is in their appearance. They are translucent and blend in with the skin, which makes them more useful for cosmetic surgery. In some cases, the incision may be seen through the tape, using a powerful light, which may avoid the need to remove the tape during routine examinations.

What is claimed is:

1. In a wound closure tape comprising a nonwoven fabric having a pressure-sensitive adhesive uniformly disposed over one surface thereof, the improvement wherein the nonwoven fabric comprises a web of continuous thermoplastic filaments that are randomly disposed in the plane of the web and bonded in an intermittent pattern of emboss bonded areas, said filaments being substantially free of interfilament bonding except in said emboss bonded areas, and wherein said tape having a width of from ¼ inch to ½ inch has a stress at 20% elongation of from about 4 to 8 pounds/inch width.

2. The tape of claim 1 wherein the nonwoven fabric is a polyamide fabric.

3. The tape of claim 1 wherein said pattern of emboss bonded areas comprises intermittent areas that are generally rectangular in shape, with the individual rectangles having one dimension longer than the other, and with the rectangular areas being arranged such that rectangular areas whose long dimensions are oriented in a first direction alternate in both said first direction and a second direction normal to said first direction with rectangular areas whose long dimensions are oriented generally in said second direction.

4. The tape of claim 3 wherein the nonwoven fabric is a polyamide fabric.

5. The tape of claim 2 wherein the nonwoven fabric includes an anti-static agent.

6. The tape of claim 4 wherein the nonwoven fabric includes an anti-static agent.

* * * * *